(12) United States Patent
Tatem, Jr.

(10) Patent No.: US 7,346,133 B2
(45) Date of Patent: Mar. 18, 2008

(54) AUTOMATED FREQUENCY COMPENSATION FOR REMOTE SYNCHRONIZATION

(75) Inventor: James E. Tatem, Jr., Kirkland, WA (US)

(73) Assignee: Harris Corporation, Melbourne, FL (US)

( * ) Notice: Subject to any disclaimer, the term of this patent is extended or adjusted under 35 U.S.C. 154(b) by 431 days.

(21) Appl. No.: 10/772,441

(22) Filed: Feb. 6, 2004

(65) Prior Publication Data

US 2004/0155685 A1 Aug. 12, 2004

Related U.S. Application Data

(62) Division of application No. 09/488,313, filed on Oct. 20, 2000, now Pat. No. 6,823,031.

(51) Int. Cl.
*H04L 27/06* (2006.01)
*H03D 3/24* (2006.01)

(52) U.S. Cl. .................................. 375/344; 375/376

(58) Field of Classification Search ........ 375/371–376, 375/326, 316, 344; 327/131, 137, 141–159
See application file for complete search history.

(56) References Cited

U.S. PATENT DOCUMENTS

| | | | |
|---|---|---|---|
| 4,325,023 A * | 4/1982 | Zirwick | .................... 324/76.19 |
| 4,546,322 A * | 10/1985 | Crutcher | ...................... 329/308 |
| 4,747,160 A | 5/1988 | Bossard | |
| 5,420,851 A | 5/1995 | Seshadri et al. | |
| 5,440,266 A * | 8/1995 | Ono | ............................ 329/307 |
| 5,499,393 A | 3/1996 | Fukui | |
| 5,768,254 A | 6/1998 | Papadopoulos et al. | |
| 5,786,778 A | 7/1998 | Adams et al. | |
| 5,809,431 A | 9/1998 | Bustamante et al. | |
| 5,828,695 A | 10/1998 | Webb | |
| 5,890,055 A | 3/1999 | Chu et al. | |
| 5,914,592 A * | 6/1999 | Saito | ....................... 324/121 R |
| 5,936,565 A | 8/1999 | Bogdan | |
| 5,963,608 A * | 10/1999 | Casper et al. | ................ 375/373 |
| 6,006,069 A | 12/1999 | Langston | |
| 6,011,818 A | 1/2000 | Yang | |
| 6,016,311 A | 1/2000 | Gilbert et al. | |
| 6,282,249 B1 | 8/2001 | Tomesen et al. | |
| 6,463,266 B1 | 10/2002 | Shohara | |

* cited by examiner

*Primary Examiner*—Tesfaldet Bocure
(74) *Attorney, Agent, or Firm*—Duane Morris LLP

(57) ABSTRACT

Systems and methods for providing frequency compensation over a wide range of frequency drift are shown. The preferred embodiment utilizes a sweep mode function to provide frequency compensation over a range of frequency drift broader than the frequency drift accommodated by a phase lock loop, without increasing the noise characteristics of the phase lock loop. Accordingly, the preferred embodiment operates in a phase lock loop mode while frequency drift can be compensated for by the lock range of the phase lock loop circuitry. The preferred embodiment operates in sweep mode to step through a range of offset frequencies to position the phase lock loop mode where frequency drift can be compensated for by the lock range of phase lock loop circuitry. Additionally, a preferred embodiment of the present invention includes a drift mode in order to monitor frequency offset information, such as may be used in performing sweep mode functions and/or other control or management functions.

6 Claims, 2 Drawing Sheets

AUTOMATED FREQUENCY COMPENSATION FOR REMOTE SYNCHRONIZATION

RELATED APPLICATIONS

The present application is a divisional of, claims benefit of, and is with commonly assigned U.S. patent application Ser. No. 09/488,313, filed Oct. 20, 2000 now Pat. No. 6,823,031, entitled "Automated Frequency Compensation for Remote Synchronization", which is related to and co-pending with commonly assigned U.S. patent application Ser. No. 08/740,332, now Pat. No. 6,016,313, entitled "System and Method for Broadband Millimeter Wave Data Communication", and its co-pending and commonly assigned divisional patent applications Ser. No. 09/434,832, now Pat. No. 7,054,289, entitled "System and Method for Broadband Millimeter Wave Data Communication", 09/434,815, now Pat. No. 6,735,452, entitled "System and Method for Broadband Millimeter Wave Data Communication", 09/434,816, now Pat. No. 6,748,240, entitled "System and Method for Broadband Millimeter Wave Data Communication", and 09/434,707, now Pat. No. 6,778,516, entitled "System and Method for Broadband Millimeter Wave Data Communication", and to co-pending and commonly assigned U.S. patent application Ser. No. 09/267,055, now Pat. No. 6,573,808, entitled "Millimeter Wave Front End", the disclosures of which are hereby incorporated herein by reference.

TECHNICAL FIELD

The present invention relates generally to the synchronization of two or more systems and more particularly to systems and methods for providing a low noise clock at a remote communication system which closely matches a master reference clock in another system in communication therewith.

BACKGROUND

In providing wireless communication using radio frequency modulated signals, it is desirable to enable two systems in communication, such as a remote system and a centralized communication hub such as shown in the above referenced patent applications entitled "System and Method for Broadband Millimeter Wave Data Communication," to operate tuned to a same RF channel with a certain amount of accuracy in order to provide for reliable acquisition of signal information communicated. Moreover, it is generally desired that the systems and methods utilized to provide this frequency synchronization be able to accommodate frequency drift, or other inaccuracies, associated with design tolerances of components, temperature variations, and/or aging of components as well as to efficiently utilize resources.

Solutions have been developed which attempt to lock up, i.e., automatic frequency compensation (AFC), a remote clock to either a carrier signal that is transmitted from the source or try to lock up to a recovered clock, something that is extracted from the data. For example, one solution has been to use a dotting pattern, i.e., particular bits are placed in the data stream at predetermined positions, in order to allow a remote communication system recover a host clock. A problem with either of these techniques is that they usually provide a very limited lock range, so overall performance due to aging and drift from temperature can be unreliable. As long as the system is properly initialized and running, it will generally operate acceptably within the designed lock range. However, after such a system has been in operation for an extended period of time, it can no longer compensate for drifts beyond some point. Accordingly, if the system requires restarting or reinitialization, especially after the components have aged and thus their operating parameters have drifted, the system may not be able to reacquire the clock signal.

Although it might seem straight forward to enlarge the window of the lock range in which such a system may operate, such an endeavor inevitably leads to a trade off in the frequency characteristics of the system. Specifically, when the lock range over which the clock signal, such as a dotting pattern or the carrier frequency, may be acquired remotely generally results in the increase in phase noise associated with the reference oscillator used, i.e., the effect of the error or noise associated with the frequency versus time characteristics of the oscillator are inversely proportional to the range of frequencies over which the oscillator is used to acquire the signal. Phase noise contributes to the RF carrier through the relation 20 log(RF out frq/base osc freq) At relatively high frequencies, such as the millimeter wave (mmwave) frequencies of the above referenced patent applications entitled "System and Method for Broadband Millimeter Wave Data Communication," an even slight increase in phase noise can cause undesired results, such as increased bit error rate (BER).

Moreover, the phase noise characteristics may become even more important in systems utilizing certain relatively high frequency, such as millimeter wave, front ends, such as embodiments shown in the above referenced patent application entitled "Millimeter Wave Front End," wherein a same reference oscillator is utilized for various functions. Where the oscillator output is multiplied up to drive the millimeter wave front end as well as used in signal acquisition at an intermediate frequency, a small increase in phase noise at the oscillator may be unacceptable at the radio frequencies and/or intermediate frequencies used. For example, in a system using a 15 MHZ reference frequency multiplied up to provide a 40 GHz mmwave front end, the phase noise of the reference oscillator is magnified over 2500 times, i.e., 20 log (40 GHz/15 MHz)=20 log (2666) =68.5 dB.

Another solution to providing frequency synchronization between two systems in communication is to provide a very precise oscillator, such as may be tuned and calibrated prior to deployment, in each of the systems in order to ensure that the remote unit will always operate within a selected range of the other system. A very narrow band phase lock loop (PLL) may be employed in such a system to accommodate any small amount of drift associated with such oscillators. However, oscillators which may be relied upon to provide such very precise reference frequencies are generally very expensive and, thus, typically do not provide a desirable alternative.

Other solutions have included the use of a dual mode phase lock loop such that the phase lock loop operates in a wide band mode that can acquire the system signal to some degree and, once it locks in at a course range, narrows the loop bandwidth of the phase lock loop. Such a system relies upon the more fine bandwidth of the second mode of the phase lock loop to filter out phase noise. However, experimentation has revealed that the phase noise associated with the wide lock range of the first mode of the dual modes does not provide a reliable lock, particularly at higher frequencies such as millimeter wave frequencies, from which the second mode may operate.

Accordingly, a need exists in the art for systems and methods providing frequency compensation over a relatively large range of frequencies. Moreover, a need exists in the art for such systems and methods to provide such frequency compensation with a very low phase noise associated therewith.

A further need exists in the art for systems and methods providing remote synchronization using frequency compensation techniques to provide accurate frequency synchronization efficiently. Efficiency considerations include not only the cost of components employed in the frequency compensation techniques, but also the ability to minimize the components used and/or to utilize inexpensive components in other portions of the communication system.

SUMMARY OF THE INVENTION

These and other objects, features and technical advantages are achieved by a system and method which provides AFC to provide a low noise clock that very closely matches a master reference clock in another system. According to the preferred embodiment, error between the local clock and the master clock is minimized while a low noise figure is maintained. Moreover, to allow for the use of relatively inexpensive system components, the affects of extreme temperatures, and/or extended operation, the preferred embodiment provides a relatively large, i.e., very tolerant, lock range.

According to a preferred embodiment of the present invention, AFC is provided using a relatively low cost voltage controlled oscillator (VCO), or other controllable oscillator. For example, a preferred embodiment of the present invention uses a Murata TV2178 VCO which is approximately ⅛ the cost of a precision OCXO. However, the Murata part has an aging spec 20 times greater (worse) that a precision part and thus would typically provide a less desirable clock signal.

The oscillator is preferably controllable both to acquire frequency synchronization over a relatively wide range of frequencies and to maintain frequency synchronization during system operation. To accommodate a wide range of offsets between a nominal frequency and the local oscillator, such as the above mentioned VCO, and the master clock to which a matching frequency is sought, a control function is preferably provided, referred to herein as a sweep function, which steps through various operating states of the VCO. This combination produces a very low phase noise clock source that can track frequency offsets automatically with high precision and maintain a wide acquisition range.

Sweep mode is preferably a decision directed control loop. Accordingly, it is better suited to microprocessor control, than a traditional DPLL. The decision that drives the control can be made over very long time intervals and accommodate user intervention more easily, e.g., preferred embodiments of the present invention can differentiate first time installation from an in-service loss of signal, or outage.

In a preferred embodiment, control of the oscillator is provided digitally. For example, a digital to analogue converter (DAC), and digital phase lock loop (DPLL) control circuit are coupled to a VCO of a preferred embodiment to provide control of an oscillator according to the present invention. Accordingly, a low cost oscillator can be augmented with low cost digital components to provide a solution that is less expensive than a high precision, high stability oscillator.

A preferred embodiment of the present invention provides at least three modes of operation to provide for synchronization of frequencies over a broad range and to maintain synchronization throughout operation. According to a most preferred embodiment, the modes of operation include phase lock loop operation, sweep mode operation, and drift compensation operation. Of course, it should be appreciated that the modes of the preferred embodiment may be used in combination with other operational modes and/or in exclusion of ones of the operational modes described herein.

In the preferred embodiment, during phase lock loop operation, systems of the present invention operate as a typical phase lock loop well known in the art. Accordingly, a signal, such as may be recovered from a receiver, is used as a timing reference and a controllable oscillator, such as a VCO, is adjusted to match a common denominator with the reference signal.

Preferably, phase lock loop functionality is provided digitally (DPLL). The preferred embodiment DPLL calculates a digital value that is written to a DAC for conversion to an analogue voltage for control of the VCO. Preferably, the DPLL control circuit updates the VCO control value very frequently, such as on the order of microseconds. The DPLL also preferably has a lock detect function.

The sweep mode of the preferred embodiment operates to adust the controllable oscillator to a particular setting, such as by the above described digital control writing a value to the VCO's control DAC, and then monitors operation of the system, such as to monitor a recovered data signal to identify a specific pattern in the data signal. If monitoring of the system does not indicate a desired result, such as identification of the specific pattern in the recovered data signal, the oscillator is adjusted to a next increment. Operation of the sweep mode to adjust the oscillator preferably includes adjustment both above and below a nominal frequency.

Preferably, monitoring of the system is performed for a preselected amount of time determined to be sufficient to reliably detect the desired condition and brief enough to provide an efficient sweep operation. The selection of operating parameters, such as the incremental size of the oscillator adjustment step, the dwell time, and the range of the steps performed in the sweep mode are preferably dependant on the greater system the AFC circuit is operating within. After the iterative adjustment of the oscillator, the operation of the system is again monitored, continuing as described above until the desired result is detected. Once the system has detected the desired condition, such as a pattern match, it is determined that the oscillator is within the lock range of the PLL and, thus, control is preferably turned over to the above described PLL.

It should be appreciated that operation of the sweep mode as described above allows the use of a narrow band phase lock loop, thus having a low phase noise associated therewith, with a heuristic step approach to provide a wide lock range. Accordingly, an acceptable offset range may be selected with respect to a nominal frequency over which frequency synchronization is to be achieved. This range may be divided into steps, such as incremental steps associated with the lock range of the phase lock loop used. This may, for example, give 10 steps above the nominal frequency and 10 steps below the nominal frequency. Thereafter, the operation of the oscillator and its associated phase lock loop may be swept through these 20 steps, or some subset thereof, sequentially to determine if the phase lock loop is able to achieve a lock at any of these steps.

It shall be appreciated that the sweep mode of the present invention is better suited for applications where a low frequency master clock is utilized with a very high frequency RF, such as in a 40 GHz mm wave system using a 15 MHz IF then is a dual mode PLL. This is because the large multiplicative factor from the reference clock to the RF is too much for even a wide band PLL. In such implementations the IFs are stable and the base clock cannot be recovered reliably.

The drift compensation mode of the preferred embodiment monitors the adjustment values of the oscillator, such as the above mentioned DAC values, while the system is operating. Preferably, while the oscillator is operational under control of the PLL and synchronized with the master clock, the drift compensation mode periodically reads and stores information with respect to the adjustment of the oscillator. It should be appreciated that the control information which achieves a lock in the PLL may vary due to a number of factors, such as local oscillator drift, master clock oscillator drift, thermal drift, and general aging in other reference components in the system, e.g. voltage references. By monitoring and recording the control information of the oscillator during its operation, this information may be utilized as a starting value for functions such as the aforementioned sweep mode. For example, the sweep mode may be required throughout the life of the system for a number of reasons, such as interruption of service due to a service call, a power outage, or any interruption between the master system and the remote system. Additionally, operation of the sweep mode may be required if the PLL becomes unlocked and cannot recover a lock independently.

The oscillator control information monitored by the drift compensation mode may additionally or alternatively be utilized for statistical functions, predictive determinations, alarm conditions, or like control functions. For example, the monitored DAC values may be compared to previous DAC values to determine if the value is drifting over time. Where the drift is determined to be unacceptably rapid or approaching an operational limitation, for example, an alarm condition may be set to forewarn a predicted system malfunction.

A technical advantage of the present invention is that an inexpensive controllable oscillator, such as an inexpensive VCO having a DAC coupled thereto to drive the control voltage, may be utilized to provide reliable remote synchronization of a frequency over a relatively large drift range.

A further technical advantage of the present invention is provided in implementing the AFC with a substantially standard PLL having a very narrow loop bandwidth. This provides a desired low phase noise characteristic in a relatively inexpensive and simple to implement system.

A still further technical advantage is provided by the present invention in a sweep mode operation that allows the oscillator to be stepped through various operating settings and provide the ability to hunt through a given spectrum, such as either side of a selected nominal frequency, for the lock range at which a PLL can then lock onto the master clock.

A yet further technical advantage is provided by the ability of the present invention to provide statistics useful for performance monitoring and trouble shooting.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWING

For a more complete understanding of the present invention, and the advantages thereof, reference is now made to the following descriptions taken in conjunction with the accompanying drawing, in which.

DETAILED DESCRIPTION

Figure 1:
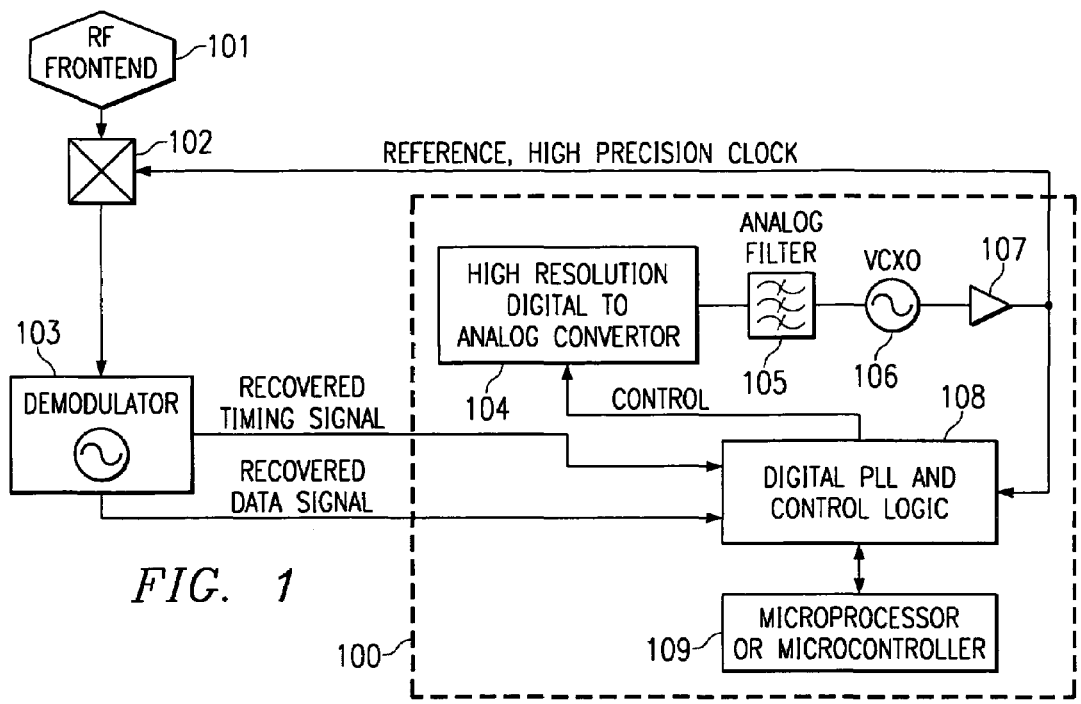
FIG. 1 shows a high level block diagram of a preferred embodiment system of the present invention.

Directing attention to FIG. 1, an RF receiver circuit adapted according to the present invention is shown having RF front end 101 and demodulator 103. Automatic frequency control (AFC) 100 of the present invention is coupled to a received signal provided by RF front end 101 by mixer 102 to allow demodulator 103 to recover information modulated with a particular carrier frequency. Accordingly, in the preferred embodiment of FIG. 1, a local VCO, which provides a reference frequency, is used to tune a receiver based on a recovered timing signal from the demodulator.

The preferred embodiment AFC 100 of FIG. 1 includes DAC 104, filter 105, VCO 106, clock signal generator 107, DPLL and control logic 108, and controller 109. VCO 106 provides a controllable reference frequency and is coupled to clock signal generator 107 to operate therewith to provide a controllable clock signal. This controllable clock signal is preferably provided to RF circuitry, such as through mixer 102, to provide a signal synchronized with a master clock, or some common denominator thereof, utilized in generating the transmitted RF signal.

It should be appreciated that the clock signal of clock signal generator 107 may be provided to circuitry other than that directly responsible for recovery of the transmitted information. For example, the clock signal may be provided to control circuitry, such as included with DPLL and control logic 108 of the preferred embodiment, to provide comparison with a recovered timing signal or other such function. Additionally, or alternatively, the clock signal may be provided to circuitry outside the control loop, such as RF front end 101. For example, the clock signal provided by clock signal generator 107 may be multiplied, or otherwise manipulated, to tune the RF front end to a particular air link RF frequency which is stepped down to an intermediate frequency (IF), such as may be utilized at mixer 102 and/or demodulator 103.

According to the preferred embodiment, VCO 106 is controlled by DPLL and control logic 108 through DAC 104. In the preferred embodiment filter 105 is provided in the signal path between DAC 104 and VCO 106 in order to ensure the application of a clean control signal to VCO 106. Of course the use of such a filter may be omitted, if desired.

In the preferred embodiment, DAC 104 is a high resolution digital to analogue convertor to provide precise control of VCO 106. For example, DAC 106 may be a 12 or 16 bit DAC to provide 4096 or 65536 control states respectively. Of course the level of granularity of the control provided with respect to the oscillator according to the present invention may be adjusted to be greater or less than that described above, depending upon the particular implementation.

It should be appreciated that the use of digital control of the oscillator of the present invention is not a limitation of the invention and may be foregone. However, the preferred embodiment utilizes digital control due to the widespread availability of digital logic circuits capable of being programmed, or otherwise operated, to perform the control functions of the present invention. The use of such digital control circuitry is further advantaged due to the inexpensive and relatively precise control interface to inexpensive oscillators available through the use of digital to analogue conversion. Of course, where an oscillator is utilized which presents a digital interface, use of the DAC of the preferred embodiment may be omitted, if desired.

A preferred embodiment of the present invention provides at least three modes of operation to provide for synchronization of frequencies over a broad range and to maintain synchronization throughout operation. For example, a preferred embodiment of the present invention provides operation in a phase lock loop, preferably DPLL, mode, sweep mode, and drift compensation mode.

Preferably, during phase lock loop operation, DPLL and control logic 108 provides phase lock loop functionality which is well known in the art to synchronize the clock signal of clock signal generator 107 with a master clock associated with the received signal. Accordingly, in the normal operational state of AFC 100, DPLL and control logic 108 will operate to synchronize the clock signal of clock signal generator 107 with the master clock. Specifically, DPLL and control logic 108 will monitor the recovered timing signal, which may be a bit pattern and/or which may be a comparison of the received signal, or a portion thereof, and the generated clock signal, and determine a control value associated with VCO 106 suitable for maintaining synchronization of the clock signal with the master clock. Control bits of the control signal are provided by DPLL and control logic 108 to DAC 104 to thereby provide a proper control voltage to VCO 106.

It should be appreciated that a typical PLL, such as a DPLL of DPLL and control logic 108, and VCO trade off lock range for noise performance. However, the present invention allows the use of a PLL having a relatively narrow lock range, and therefore a low phase noise, and yet still provide operation over a relatively large overall lock range. Specifically, the control logic can sweep for large frequency offsets that may occur due to aging, poor calibration, temperature, or other conditions. In systems that require long field service, the offsets can be very significant. Once the reference source is acquired, the PLL can fine tune and maintain lock while maintaining low noise requirements.

The lock range of DPLL and control logic 108 is selected so as to accommodate a reasonable amount of frequency drift under the expected operational conditions without introducing an unacceptable amount of phase noise into the system. For example, where the clock signal of clock signal generator 107 is utilized in tuning a high frequency RF front end, such as on the order of 38 GHz, and also to provide locking at an IF frequency, such as on the order of 500 MHZ, only a very small amount of phase noise will be tolerable.

Whenever DPLL and control logic 108 is unable to acquire or maintain a lock on the master clock in phase lock loop mode, i.e., the amount of frequency drift is beyond the range of drift accommodated by the DPLL, controller 109 will preferably operate to control DPLL and control logic 108 in a sweep mode. The sweep mode of the preferred embodiment, as discussed in detail with reference to FIG. 2 below, operates to adust VCO 106 to a particular setting by DPLL and control logic 108 writing a value to DAC 104, and then monitoring a recovered data signal to identify a specific pattern. If monitoring of the system does not indicate identification of the specific pattern in the recovered data signal, VCO 106 is adjusted to a next increment. Accordingly, controller 109 will provide instructions to DPLL and control logic 108 to step through various offsets of a nominal frequency in order to determine a frequency at which the DPLL lock range is capable of acquiring synchronization. In the preferred embodiment, the modulator is free running during operation of the sweep mode and is looking for a signal. Demodulated signals are fed into the control logic of DPLL and control logic 108 which preferably does pattern matching to detect frequency synchronization. DPLL and control logic 108 control logic signals the microprocessor when the correct pattern is detected in order to cease operation of the sweep mode.

Preferably, when the system is initially commissioned, the controller defaults to a particular value that will begin the sweep mode by locking the VCO at a predetermined frequency, such as a frequency approximately in the center of the operating range of the circuit. However, in the preferred embodiment, after initial commissioning, DPLL and control logic 108 operates in a drift mode which records frequency offset information to allow subsequent iterations of the sweep mode to begin at a VCO control value very near the last operational value.

According to the preferred embodiment, monitoring of the system is performed for a preselected amount of time determined to be sufficient to reliably detect the desired condition and brief enough to provide an efficient sweep operation. The selection of operating parameters, such as the incremental size of the oscillator adjustment step, the dwell time, and the range of the steps performed in the sweep mode are preferably dependant on the greater system the AFC circuit is operating within. For example, dwell time may be established to correspond to a particular number of modem data frames, i.e., 4 modem data frames of 1 sec each to provide a dwell time of 4 secs.

After the iterative adjustment of the oscillator, the operation of the system is again monitored, continuing as described above until the desired result is detected. Once the system has detected the desired condition, such as a pattern match, it is determined that the oscillator is within the lock range of the PLL and, thus, control is preferably turned over to the above described PLL.

It should be appreciated that operation of the sweep mode as described above allows the use of a narrow band phase lock loop, and thus having a low phase noise associated therewith, with a heuristic step approach to provide a wide lock range. Accordingly, an acceptable offset range may be selected with respect to a nominal frequency over which frequency synchronization is to be achieved. This range may be divided into steps, such as incremental steps associated with the lock range of the phase lock loop used. This may, for example, give 10 steps above the nominal frequency and 10 steps below the nominal frequency. Thereafter, the operation of the oscillator and its associated phase lock loop may be swept through these 20 steps sequentially to determine if the phase lock loop is able to achieve a lock at any of these steps.

The drift compensation mode of the preferred embodiment monitors the above mentioned DAC values while the system is operating. Preferably, while VCO 106 is operational under control of the PLL and synchronized with the master clock, the drift compensation mode periodically reads and stores the DAC values, such as for use in subsequent sweep mode operations.

The oscillator control information monitored by the drift compensation mode may additionally or alternatively be utilized for statistical functions, predictive determinations, alarm conditions, or like control functions. Accordingly, additional information may also be stored by controller 109, such as a historical progression of DAC values and possibly the rate at which the values have changed historically. Such information may be utilized in predicting future drift and/or in more rapidly acquiring frequency lock after a loss of service. Processor 109 may also store information with respect to an amount of change of VCO control information for particular periods of time, such as to determine impending system malfunction and/or anomalous system operation.

Using the above described monitored and/or stored information, the control logic of the present invention is able to determine how the phase lock loop and/or oscillator are performing. For example, if the DAC control value is not changing rapidly in the short term, such as in a period of a couple seconds, then a determination may be made that the system is frequency locked. However, if the DAC control value is changing frequently, such as within a period of a couple of seconds, then a conclusion may be reached that the system is not frequency locked or that there is something wrong. If the DAC control value is varying slowly, such as over a period of a couple of days, then a determination may be made that there is a problem with the VCO in the way it is locking up to the master clock. If the DAC value is drifting out towards the higher ends of the range of the DAC, it may be determined that there is a problem with the VCO and its ability to frequency lock in the future, which may signify a maintenance issue requiring an alarm.

In determining how the phase lock loop and/or oscillator are performing, information may be monitored in a number of different ways. For example, to determine if the unit is actually frequency locked, the DAC control information, or other oscillator control information, may be read multiple times in relatively close succession, such as once a second four times in a row. If the same value is read for each of these iterations, or possibly even for some majority of these iterations, then it may be determined that frequency lock is being maintained. During frequency lock, it may be desired to read the control value periodically, such as once every few minutes, to provide an operating mean or average, or other statistical information. This information, such as the average value over a predetermined period of time, may be stored to be used as an initial value in the sweep mode, for example. This value may be updated periodically, such as on a daily basis. Daily maintenance of this stored value may be excessive in particular implementations, however the preferred embodiment utilizes such relatively frequent maintenance to allows tracking long term drift, such as to provide warning of maintenance or reliability problems.

Figure 2:
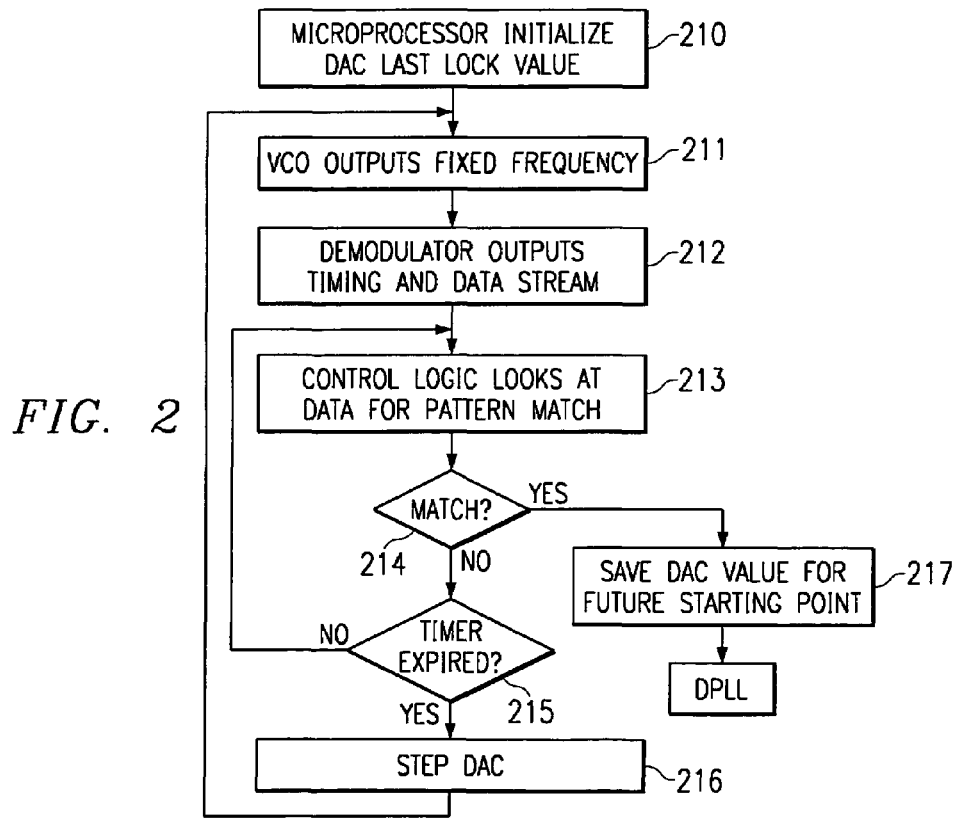
FIG. 2 shows a flow diagram of the operation of a preferred embodiment of the sweep mode of the present invention.

To better understand the operation of AFC 100 it is helpful to reference the flow diagram of FIG. 2 showing the sweep mode operation of the preferred embodiment AFC in more detail. In starting the sweep mode at step 210, the microprocessor digital control will preferably initialize the DAC at the last lock value, where one is known, or at a value determined to be a suitable starting point, such as a center frequency of the operating range. For example, where there is no previous lock value, such as at system commissioning, an initial value may be loaded from a factory setting.

At step 211, the VCO is operated at a fixed frequency based on the DAC value. The demodulator will be receiving a signal from the RF front end and will output the timing signal and the data stream information it is able to demodulate from the received signal having the clock signal associated with the selected DAC value applied thereto (step 212). It should be appreciated that where the clock signal is substantially out of synchronization with the master clock, i.e., offset from the carrier frequency such that the demodulator cannot acquire the transmitted information, the timing signal and data stream information will be pseudo random information.

The digital control logic will monitor the information provided by the demodulator outputs, such as by attempting to match a data pattern contained therein to an existing or pre-known data pattern (step 213). If the digital control logic detects a match at step 214, the DAC value will preferably be stored for future iterations of the sweep mode at step 217, and operation of the sweep mode ends in favor of DPLL operation.

If a match is not detected at step 214, a determination is made as to whether a timer has expired at step 215. If the timer has not expired, processing returns to step 213 wherein the information continues to be monitored. Accordingly, operation of the sweep mode monitors the information provided by the demodulator for a set period of time, such as a period of time determined to be sufficient to reliably detect a predetermined bit pattern, before adjusting the clock frequency.

However, if the timer is determined to have expired at step 215, processing proceeds to step 216 wherein the DAC is stepped to a next control value by the microprocessor and the controller and processing is returned to step 211 wherein the VCO is adjusted to operate at the selected control value. The operation of the sweep function will thereafter continue the search for a frequency lock as described above.

In a preferred embodiment the step increments of the VCO control value is 0.2 ppm. However, any step amount deemed to be suitable for a particular implementation may be utilized. Generally, it is desired to select a step increment amount which is either equal to or slightly less than the lock range of the PLL in order to adequately scan the full lock range of the system. However, other step schemes may be utilized including step increments of varying size, such as may be utilized to rapidly scan particular VCO settings determined to have a greatest likelihood of achieving a lock, followed by a more thorough sweep if frequency lock is not achieved.

It should be appreciated that stepping of the DAC to a next control value preferably includes adjustment both above and below a nominal frequency. For example, the initial value selected for the DAC at step 210 is preferably a value at which the DPLL is most likely to achieve frequency lock, i.e., the last known lock value. However, if a lock is not achieved, it would be uncertain whether the selected value is too high or too low. Accordingly, the preferred embodiment will operate to step the VCO both upward and downward so as to address possible drift in either direction.

Preferably, in order to achieve a lock as quickly as possible, stepping of the VCO in each direction is interleaved, i.e., a first value higher than the nominal value is tested, followed by a first value lower than the nominal value, followed by a second value higher than the nominal value, and so on. Of course, such an interleaved technique may not always provide the most efficient sweeping of the possible values. For example, where DPLL and control logic 108 is utilized to store information regarding control values over time, it may be determined that the VCO offset has historically drifted in a particular direction, i.e., drifted toward higher frequencies. Accordingly, controller 109 may determine that it is desired to first step thorough a range of higher values first followed by a range of lower values.

Various boundary conditions may be established in the sweep function described above. For example, a determination may be made as to the maximum excursions from the center frequency that the VCO could reliably lock, in order to set outer boundaries on the sweep function. Additionally or alternatively boundaries may be established for a particular sweep operation, such as establishing a sweep range of +/−2 ppm of the last lock value.

Figure 3:
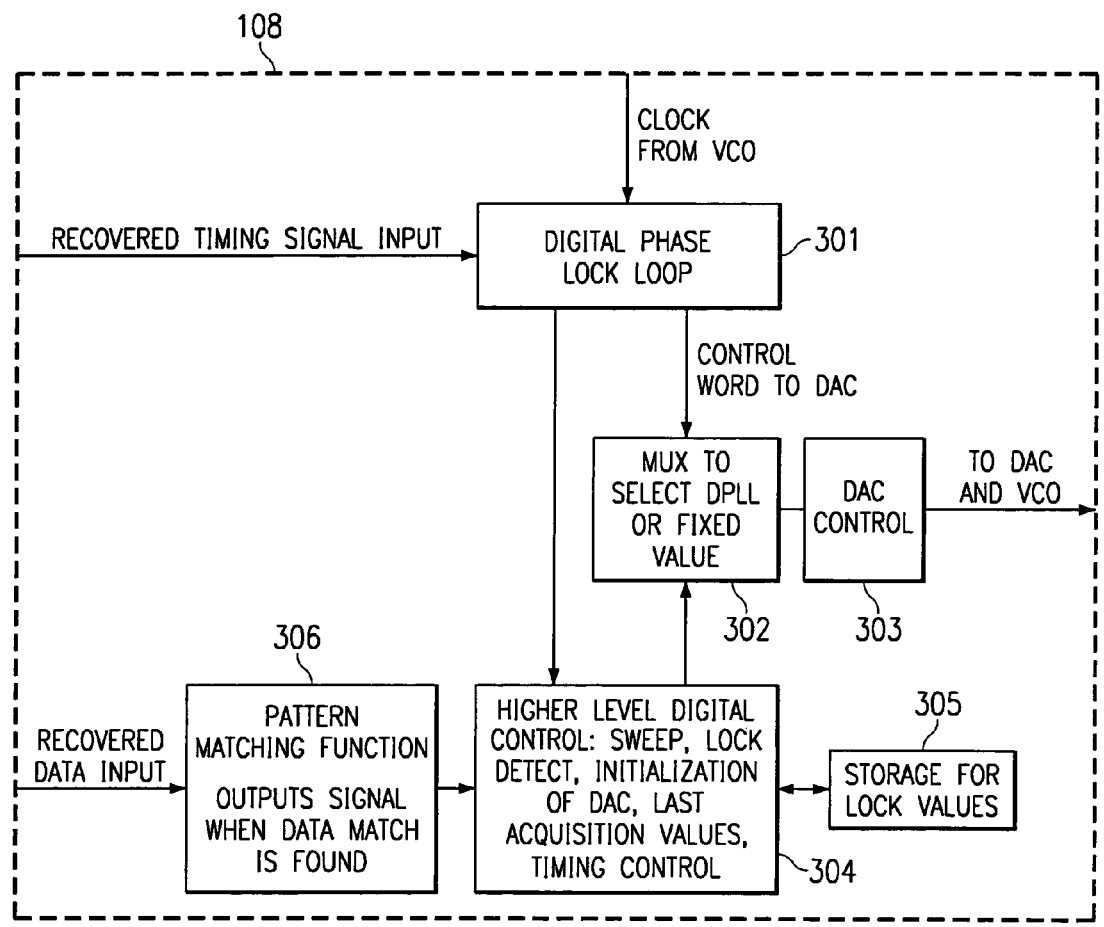
FIG. 3 shows a block diagram of a preferred embodiment phase lock loop and control circuit of the system of FIG. 1.

FIG. 3 provides a more detailed look at the preferred embodiment DPLL and control logic 108 of FIG. 1. As described above, the preferred embodiment DPLL and control logic 108 provides several functions. Specifically, there is the digital phase lock loop function, illustrated as DPLL 301, which is used when the VCO circuit is in normal control mode, such as after a frequency lock has been achieved through the above described sweep function. Preferably, DPLL 301 controls VCO 106 to keep VCO 106 locked up to recover the timing signal in demodulator 103. For example, in a preferred embodiment the VCO clock, the reference clock in DPLL 301, is divided down to a frequency common to the recover timing signal, such as approximately 8 KHz, and the recovered timing signal input into DPLL 301 is divided down to this common frequency for a comparison of the edges of those two lower frequency clocks. When DPLL 301 is able to control VCO 106 to maintain a match between VCO 106 and the recovered timing signal, DPLL and control logic 108 is operating in DPLL mode.

In the preferred embodiment, a multiplexer, such as MUX 302, is provided in the signal path between DPLL 301 and DAC 104. MUX 302 provides a convenient means by which control of VCO 106 may be assumed by control functions in addition to DPLL 301. For example MUX 302 provides an interface that allows a microprocessor, such as controller 109, or any other higher level digital control logic to feed values into DAC 104, such as for the sweep function of the present invention.

Also shown in the signal path between DPLL 301 and DAC 104 is DAC control 303 which, in the preferred embodiment, provides latching or buffering of the DAC control signals provided by DPLL 301 and/or any other control source. DAC control 303 may be utilized to maintain DAC/VCO control signals between control word calculative iterations of DPLL 301, for example. Additionally or alternatively, DAC control 303 may be utilized to buffer rapid control word changes, to provide hysteresis dampening or otherwise address undesired circuit responses.

In a preferred embodiment, where DPLL 301 is operable over a range significantly less than that of the sweep mode, DAC control 303 may be utilized to latch most significant bits of the VCO control word from control information provided by control logic, such as control logic 304, and to accept VCO control information from DPLL 301 as least significant bits to the control word. Accordingly, DPLL 301 is enabled to control VCO 106 throughout a much larger range, albeit within a sliding window controlled by the sweep function of the present invention, without requiring alteration of the DPLL such as might introduce a larger than acceptable phase noise figure.

Control logic 304 provides high level control of DPLL and control logic 108, such as for sweep functions, frequency lock detection, initialization of the DAC, monitoring and recording of last acquisition values, timing control, and the like. Accordingly, control logic 304 is coupled to various of the components of DPLL and control logic 108 and, in essence, provides an interface to the rest of the system. For example, control logic 304 is coupled to DPLL 301 to receive frequency lock information therefrom. When it is detected that DPLL 301 cannot achieve a frequency lock, control logic 304 may provide overriding VCO control signals to MUX 302, through a link between control logic 304 and MUX 302, to thereby operate in sweep mode.

It should be appreciated that control logic 304 may include a processor, such as a microprocessor or central processing unit, or other control logic implementation, such as a application specific integrated circuit (ASIC) or system on a chip (SYOC). Depending upon the level of processing provided in control logic 304, controller 109 of FIG. 1 may be eliminated, if desired. Of course, controller 109 may be provided, irrespective of the processing provided in control logic 304, where its use to control other system functions is desired. Accordingly, there may be an interface (not shown) between control logic 304 of FIG. 3 and controller 109 of FIG. 1. Such an interface may allow control logic 304 to report an inability of DPLL 301 to achieve frequency lock to controller 109 which may then respond with control instructions to control logic 304 to retrieve a last known DAC value, such as from memory 305, to be provided to DAC 104 through MUX 302, thereby operating in sweep mode.

Memory 305 provides non-volatile storage of information, such as control information of the oscillator during its operation, this information may be utilized as a starting value for functions such as the aforementioned sweep mode. Additionally, memory 305 may store statistical, historical, predictive, or other information useful in controlling frequency lock or other operations of the system. In the preferred embodiment, memory 305 is a memory register associated with control logic 304. However, memory 305 may be any storage device suitable for storing the above described information. For example, where a large amount of historical information is stored, such as for system trouble shooting and/or predictive analysis, memory 305 may be a mass storage media device, such as a disk drive.

Preferably, correlator 306 provides recovered data correlation and/or a pattern matching feature, depending on how precise of a match between a recovered timing signal and a known or expected signal are desired. Accordingly, correlator 306 operates to provide a comparison between the data stream coming from demodulator 103 with a pre-known pattern, such as may be stored in correlator 306 or memory 305, for example. Information from correlator 306 is provided to control logic 304 to enable determinations of proper frequency lock, such as to stop a sweep function as having achieved frequency lock and/or to start a sweep function as having lost frequency lock.

It should be appreciated that a typical phase lock loop, such as DPLL 301 is only operable for a particular range. However, the present invention, such as implemented in the system of FIGS. 1 and 3, is adapted to broaden the operable range of the phase lock loop by stepping through certain frequencies under control of control logic, such as control logic 304 and/or controller 109. The operation of the present invention preferably allows operation in both a phase lock loop mode and a sweep mode, such as may be switched between using MUX 302 of the preferred embodiment.

Although the above described preferred embodiment has been discussed with reference to a recovered bit pattern for determining frequency lock, it should be appreciated that other techniques of determining frequency lock may be utilized. For example, the present invention may utilize carrier signal frequency matching or other techniques known in the art.

The hybrid digital analogue VCO of the preferred embodiment described above provides not only a low cost, high precision oscillator, but also provides more functionality than is available with prior art oscillator systems. As such, the systems and methods of the present invention are useful for any system that requires synchronization two or more devices. Accordingly, it should be appreciated that, although preferred embodiments of the present invention have been described herein with reference to wireless communications the concepts of the present invention are not limited to such systems. For example, the frequency compensation techniques of the present invention are useful in providing synchronization in wired systems, such as those using RF communication over copper, as well as light frequencies, such as used in fibre optics. Specifically, it is contemplated that wired communication systems such as those utilizing cable modems will benefit from the systems and methods of the present invention.

Additionally, although the preferred embodiments have been described with reference to the use of automatic frequency compensation to achieve a lock on a particular carrier frequency with a desired amount of accuracy, it should be appreciated that the techniques of the present invention are also applicable to provide timing synchronization with respect to other aspects of communications. For example, the synchronization techniques of the present invention may be utilized to lock up the systems in communication to support time division duplexing (TDD) and/or time division multiple access (TDMA) communication protocols.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of providing automatic frequency compensation comprising the steps of:
   providing a phase lock loop mode of operation to maintain frequency lock over a selected first range of frequency drift;
   providing a sweep mode of operation to step operation of said phase lock loop first range of frequency drift over a selected second range of frequency drift; and
   monitoring at least one of said phase lock loop mode of operation and said sweep mode of operation to determine a portion of said second range of frequency drift once said first range is successfully able to maintain said frequency lock;
   wherein the size of the first range of frequency drift is substantially equal to the lock range of the phase lock loop.

2. The method of claim 1, further comprising the step of:
   providing a controllable oscillator operable under control of said phase lock loop mode of operation and said sweep mode of operation, wherein said phase lock loop mode of operation utilizes a first control signal to control said oscillator and said sweep mode of operation utilizes a second control signal to control said oscillator.

3. The method of claim 2, wherein said oscillator is a voltage controlled oscillator.

4. The method of claim 1, further comprising the step of:
   storing at least a portion of information provided by said step of monitoring.

5. The method of claim 1 wherein said at least one of said phase lock loop mode of operation and said sweep mode of operation is stepped outside said selected first range of frequency drift through an offset range of frequencies in a predetermined number and increment size of steps until a desired pattern match of a recovered data signal is achieved, said steps including predetermined dwell time.

6. The method of claim 5 further comprising the step of returning to said phase lock loop mode of operation at a frequency within said offset range of frequencies once said desired pattern match is achieved.

* * * * *